(12) United States Patent
Zeun et al.

(10) Patent No.: US 8,153,616 B2
(45) Date of Patent: Apr. 10, 2012

(54) COMBINATION PREPARATION FOR ORAL CONTRACEPTION AND ORAL THERAPY OF DYSFUNCTIONAL UTERINE BLEEDING CONTAINING ESTRADIOL VALERATE AND DIENOGEST AND METHOD OF USING SAME

(75) Inventors: Susan Zeun, Berlin (DE); Pol Boudes, Hackettstown, NJ (US); Angelo Secci, Parsipanny, NJ (US); Jan Nedrikat, Chianti Kirkland (CA); Holger Zimmermann, Falkensee (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 685 days.

(21) Appl. No.: 11/609,705

(22) Filed: Dec. 12, 2006

(65) Prior Publication Data

US 2007/0111977 A1 May 17, 2007

Related U.S. Application Data

(63) Continuation-in-part of application No. 11/377,693, filed on Mar. 16, 2006.

(60) Provisional application No. 60/727,592, filed on Oct. 17, 2005.

(51) Int. Cl.
*A61K 31/56* (2006.01)
(52) U.S. Cl. .................................................. 514/170
(58) Field of Classification Search .................... 514/170
See application file for complete search history.

(56) References Cited

U.S. PATENT DOCUMENTS

| | | | |
|---|---|---|---|
| 3,639,600 A | 2/1972 | Hendrix |
| 3,795,734 A | 3/1974 | Rochefort |
| 3,957,982 A | 5/1976 | Lachnit-Fixson et al. |
| 4,066,757 A | 1/1978 | Pasquale |
| 4,272,270 A | 6/1981 | Higgins |
| 4,378,356 A | 3/1983 | DeJager |
| 4,390,531 A | 6/1983 | Edgren |
| 4,530,839 A | 7/1985 | Pasquale |
| 4,544,554 A | 10/1985 | Pasquale |
| 4,616,006 A | 10/1986 | Pasquale |
| 4,621,079 A | 11/1986 | Lachnit-Fixson et al. |
| 4,628,051 A | 12/1986 | Pasquale |
| 4,921,843 A | 5/1990 | Pasquale |
| 5,280,023 A | 1/1994 | Ehrlich et al. |
| 5,633,242 A | 5/1997 | Oettel et al. |
| 5,858,405 A | 1/1999 | Gast |
| 6,027,749 A | 2/2000 | Schmidt-Gollwitzer et al. |
| 6,133,251 A | 10/2000 | Dittgen et al. |
| 6,312,722 B1 | 11/2001 | Schmidt-Gollwitzer et al. |
| 6,670,350 B1 | 12/2003 | Oettel et al. |
| 6,782,282 B2 | 8/2004 | Bielefeldt et al. |
| 6,884,793 B2 | 4/2005 | Dittgen et al. |
| 6,987,101 B1 | 1/2006 | Nashed |
| 2002/0107229 A1 | 8/2002 | Dittgen et al. |
| 2004/0266745 A1 | 12/2004 | Schwanitz et al. |
| 2005/0032756 A1 | 2/2005 | Dittgen et al. |
| 2005/0282790 A1 | 12/2005 | Nashed |
| 2006/0135496 A1 | 6/2006 | DiLiberti et al. |
| 2007/0111977 A1 | 5/2007 | Zeun et al. |
| 2007/0259840 A1 | 11/2007 | Endrikat et al. |
| 2008/0125401 A1 | 5/2008 | Zeun et al. |

FOREIGN PATENT DOCUMENTS

| | | |
|---|---|---|
| BE | 823 689 | 6/1975 |
| CA | 1 090 256 | 11/1980 |
| CA | 2140011 A1 | 1/1994 |
| DE | 2 431 704 | 1/1976 |
| DE | 2 645 307 | 4/1978 |
| DE | 3 341 638 | 5/1984 |
| DE | 3 347 125 | 7/1985 |
| DE | 41 04 385 C1 | 8/1992 |
| DE | 42 24 534 A1 | 1/1994 |
| DE | 43 08 406 C1 | 6/1994 |
| DE | 4 339 934 | 11/1994 |
| DE | 43 13 926 A1 | 11/1994 |
| DE | 4 429 374 | 2/1996 |
| DE | 44 29 374 C1 | 2/1996 |
| EP | 26229 | 4/1981 |
| EP | 0 226 679 | 7/1987 |
| EP | 253607 | 1/1988 |
| EP | 0 378 373 A2 | 7/1990 |
| EP | 0 491 415 B1 | 6/1992 |
| EP | 0 696 454 A2 | 2/1996 |
| EP | 0 770 388 * | 5/1997 |
| EP | 0 770 388 A1 | 5/1997 |
| EP | 0 911 029 B1 | 4/2002 |

(Continued)

OTHER PUBLICATIONS

Chuong et al., Am J. Obstet Gynecol., 1996;175:787-792.*

(Continued)

*Primary Examiner* — San-Ming Hui
(74) *Attorney, Agent, or Firm* — Millen, White, Zelano & Branigan, P.C.

(57) ABSTRACT

The multiphase combination preparation for oral therapy of dysfunctional uterine bleeding and for oral contraception contains a first phase consisting of 2 daily dosage units, each containing 3 mg of estradiol valerate or <3 mg of estradiol; a second phase consisting of a first group of 5 daily dosage units, each consisting of a combination of 2 mg of dienogest with 2 mg of estradiol valerate or <2 mg of estradiol, and a second group consisting of 17 daily dosage units, each consisting of a combination of 3 mg of dienogest with 2 mg of estradiol valerate or <2 mg of estradiol; a third phase consisting of 2 daily dosage units, each containing 1 mg of estradiol valerate or <1 mg of estradiol; and another phase consisting of 2 daily dosage units of a pharmaceutically harmless placebos.

6 Claims, No Drawings

FOREIGN PATENT DOCUMENTS

| | | |
|---|---|---|
| EP | 0 835 114 B1 | 5/2003 |
| EP | 1 462 106 | 9/2004 |
| EP | 1 787 649 | 5/2007 |
| NL | 6 911 920 | 2/1970 |
| WO | WO-92 13539 | 8/1992 |
| WO | WO 95/07081 A1 | 3/1995 |
| WO | WO-98 04246 | 2/1998 |
| WO | WO 98/04268 | 2/1998 |
| WO | WO 98/04268 A1 | 2/1998 |
| WO | WO-98 04269 | 2/1998 |
| WO | WO 98/27929 A2 | 7/1998 |
| WO | WO-02 22110 | 3/2002 |
| WO | WO 2004/112797 A1 | 12/2004 |
| WO | WO 2005/102247 A2 | 11/2005 |
| WO | WO 2007/002862 A2 | 1/2007 |
| ZA | 8 509 892 | 7/1986 |

OTHER PUBLICATIONS

Zimmermann, et al., Drugs of Today, 1999; 35 (Suppl. C):13-26.*
Label for Femilar®, "Summary of Product Characterization," (Approved Oct. 28, 1992); Mar. 1, 2011 version—13 pages.
Watson's ANDA letter re: Natazia, Dec. 22, 2010—17 pages.
Clinical Study/Report—Amended, No. AZ94, pp. 2-8, from Endrikat Declaration, of Jan. 21, 2010.
Fruzzetti, F., et al., "Review of clinical experience with estradiol in combined oral contraceptives," Contraceptive 81 (2010) 8-15.
Hirvonen, E., et al., "New natural oestradiol/cyproterone acetate oral contraceptive for pre-menopausal women," Maturitas, 10 (1988) 201-213.
Serup, J., et al., "Effectivity and Acceptability of Oral Contraceptives Containing Natural and Artificial Estrogens in Combination with a Gestagen," Acta Obstet Gynecol Scand 60: 203-206, 1981.
Csemiczky, G., et al., "The Pharmacodynamic Effects of an Oral Contraceptive Containing 3 mg Micronized 17β-Estradiol and 0.150 mg Desogestrel for 21 Days, Followed by 0.030 mg Desogestrel Only for 7 Days," Contraception 1996: 54: 333-338.
Endrikat, J., et al., "A Twelve-Month Comparative Clinical Investigation of Two Low-Dose Oral Contraceptives Containing 20 µg Ethinylestradiol/75 µg Gestodene and 30 µg Ethinylestradiol/75 µg Gestodene, with Respect to Efficacy, Cycle Control, and Tolerance," Contraception 1997; 55: 131-137.
Endrikat, J., et al, "Multicenter, comparative study of cycle control, efficacy and tolerability of two low-dose oral contraceptives containing 20 µg ethinylestradiol/100 µg levonorgestrel and 20 µg ethinylestradiol/500 µg norethisterone," Contraception 64 (2001) 3-10.
Graser, T., et al., "Comparison of the efficacy and endometrial safety of two estradiol valerate/dienogest combinations and Kliogest® for continuous combined hormone replacement therapy in postmenopausal women," Climacteric 2000: 3: 109-118.
Graser, T., et al., "Dienogest as a Progestin for Hormone Replacement Therapy," Drugs of Today 1999, 35 (Suppl. C): 115-126.
Graser, T., et al., "Effects of a combination of 2 mg estradiol valerate and 3 mg dienogest on coagulation, lipid profile, and glucose metabolism in postmenopausal women," Drugs of Today 2001, 37 (Suppl. G): 87-99.
Graser, T., et al., "Lafamme®: A new oral preparation for continuous combined hormone replacement therapy in postmenopausal woman," Drugs of Today 2001, 37 (Suppl. G): 17-27.
Von Schoultz, B., "Clinical efficacy and safety of combined estradiol valerate and dienogest: a new no-bleed treatment," Climacteric 2003: 6 (Suppl. 2): 24-32.
Wellington, K., et al., "Estradiol Valerate/Dienogest," Drugs 2002: 62 (3): 491-504.
Rudolph, I., et al., "Influence of a continuous combined HRT (2 mg estradiol valerate and 2 mg dienogest) on postmenopausal depression," Climacteric 2004: 7: 301-311, online publication date Sep. 1, 2004, http://www.informaworld.com/smpp/title-content=t713605024.
Astedt, A., et al., "Clinical Trial of a New Oral Contraceptive Pill Containing the Natural Oestrogen 17β-Oestradiol," British J. of Ob. & Gyn., Sep. 1979, vol. 86, pp. 732-736.

Reply filed in U.S. Appl. No. 11/578,771, dated Jun. 8, 2011.
Bitzer, J., "Kontrazeption and Sexualität," Therapeutische Umschau, Band 61, 1994 Heft 2, pp. 110-114.
Davis, A., M.D., et al., "Triphasic Norgestimate-Ethinyl Estradiol for Treating Dysfunctional Uterine Bleeding," Obstet. & Gynecol., vol. 96, No. 6, Dec. 2000, pp. 913-920, XP-002317447.
Dei, M, et al., "Sex Steroids and Libido," The European Jrnl. of Contraception & Reproductive Health Care, vol. 2 (1997) pp. 253-258.
Durán, M., et al., "Effectiveness of Estradiol Valeratio/ Dienogest in the treatment of sexual function during menopause (versus study)," Acta ginecologica, vol. 63, (2006) pp. 1-8.
Endrikat, J., et al., "Ovulation inhibition with four variations of a four-phasic estradiol valerate/dienogest combined oral contraceptive: results of two prospective, randomized, open-label studies," Contraception 78 (2008) pp. 218-225.
Gräser, T., et al., "Continuous-combined treatment of the menopause with combinations of oestradiol valerate and dienogest—a dose-ranging study," Maturitas—The European Menopause Journal, 35 (2000) pp. 253-261, XP-002369505.
Gräser, T., et al., "Dienogest as a Progestin for Hormone Replacement Therapy," Drugs of Today, 1999, 35 (Suppl. C) pp. 115-126, XP-008054769.
International Search Report issued Aug. 8, 2007 in International Application No. PCT/EP2006/008626 (4 pages).
International Search Report, along with related papers, issued Jan. 4, 2007 in International Application No. PCT/EP2006/009867 (11 pages).
Kuhl, H., et al ., "Kontrazeption," 2. Völlig neubearbeitete Auflage, 19 Abbildungen, 47 Tabellen—1999 Georg Thieme Verlag, Stuttgart—New York. Cover Page and p. 140, titled 12 Kontrazeption bei Problempatientinnen.
L'Oreal's Application in the Appeal Tribunal Before: Mr. Justice Graham and Mr. Justice Whitford—Jul. 10 and 23, 1970. [No. 20] Dec. 31, 1970 [1970] R.P.C., pp. 565-579.
Moore, C., et al., "Influence of Dienogest on Ovluation in Young Fertile Women," Clinical Pharmacodynamics, Clin. Drug. Invest. 18 (4), Oct. 1999, pp. 271-278, XP-008054770.
Oettel, M., et al., "The Preclinical and Clinical Profile of Dienogest. A Short Overview," Drugs of Today, 1999, 35 (Suppl. C): pp. 3-12, XP-000909647.
Osmanağaoğlu, M.A., et al., "Effect of different preparations of hormone therapy on sexual dysfunction in naturally postmenopausal women," Climacteric, 2006; 9: pp. 464-472.
Pierson, R.A., et a l., "Ortho Evra™ /Evra™ versus oral contraceptives: follicular development and ovulation in normal cycles and after intentional dosing error," Fertility and Sterility, vol. 80, No. 1, Jul. 2003, pp. 34-42.
Rosenbaum, P., et al., "Inhibition of ovulation by a novel progestogen (drospirenone) alone or in combination with ethinylestradiol," The European Journal of Contraception and Reproductive Health Care, 2000; 5: pp. 16-24.
Saletu, B., et al., "Hormone replacement therapy and vigilance Double-blind, placebo-controlled EEG-mapping studies with an estrogen-progestogen combination (Climodien®, Lafamme®) versus estrogen alone in menopausal syndrome patients," Maturitas—The European Menopause Journal, 43 (2002), pp. 165-181.
Search Report issued Apr. 30, 2007 in ROC (Taiwan) Patent Application No. 094109222 (1 page).
Strecke, V. J., et al., "Untersuchungen zum Verhalten des Vaginalzytogramms bei Beagle-Hündinnen während toxikologischer Langzeituntersuchungen von Gestagenen[1]," Z. Versuchstierk, 24 (1982), pp. 117-125.
Taubert, H.-D., et al., "Kontrazeption mit Hormonen—Ein Leitfaden für die Praxis," 2., überarbeitete und erweiterte Auflage, 79 Abbildungen, 43 Tabellen—1995 Georg Thieme Verlag Stuttgart—New York. . Cover Page and p. 160, titled Hormanale Kontrazeptiva.
Teichmann, A.T., "Dienogest: Pre-Clinical and clinical results for the new Gestogen," Walter de gruyter, Berlin/New York, p. 101, 1995.
Timmer, C. J., et al., "Bioequivalence assessment of three different estrdiol formulations in postmenopausal women in an open, randomized, single-dose, 3-way cross-over study," European Journal of Drug Metabolism and Pharmacokinetics, 1999, vol. 24, No. 1, pp. 47-53.

Von Schoultz, B., "Clinical efficacy and safety of combined estradiol valerate and dienogest: a new no-bleed treatment," Climacteric, 2003; 6 (Suppl. 2): pp. 24-32, XP-009062446.

Wellington, K., et al., "Estradiol Valerate/Dienogest," Adis New Drug Profile, Drugs, 2002, 62(3)—Abstract, 2 pages.

Wiegratz, I., et al., "Effect of dienogest-containing oral contraceptives on lipid metabolism," Contraception, 65 (2002), pp. 223-229.

Written Opinion of the International Searching Authority issued Aug. 8, 2007 in International Application No. PCT/EP2006/008626 (6 pages).

Written Opinion of the International Searching Authority, along with related papers, issued Jul. 25, 2006 in International Application No. PCT/EP2005/004022 (28 pages).

Zimmerman, H., et al., "Pharmacokinetics of Estradiol Valerate 2mg + Dienogest 2mg (Climodien® 2/2) after Single and Repeated Oral Administration in Healthy Postmenopausal Women," Clinical Pharmacokinetics, Clin. Drug. Invest., Aug. 20, 2000, (2), Abstract (1 page).

Organon Laboratories Ltd's Application, 1970, (in English).

Awward, J. T. et al., "Abnormal uterine bleeding in the perimenopause," Int. J. Fertil., 1993, vol. 38, pp. 261-269.

Speroff et al., "Clinical Gynecologic Endocrinology and infertility," Lippincott, Williams, and Wilkins: Sixth Edition, 1999, pp. 575-593.

Fraser, I. S. et al., "Treatment of Ovulatory and Anovulatory Dysfunctional Uterine Bleeding With Oral Progestogens," Aust. Nz. J. Obetet. Gynaecol., 1990, vol. 30, No. 4, pp. 353-356.

Hickey, M et al., "Progestogens Versus oestrogens and progestogens for irregular uterine bleeding associated with anovulation," The Cochrane Database of Systematic Review, 2000, vol. 1, pp. 1-9.

Steiner, R. et al., "Abnormal Menstrual Bleeding," Schweiz Rundsch. Med. Prax., 2002, vol. 91, pp. 1967-1974.

Kuhl, H. et al., "Aktuelle Entwicklungen in der hormonalen Kontrazeption," Gynakologe, 1992, vol. 25, pp. 231-240.

Watson Pharma, Inc., "About Oral Contraceptives (OCs)," Retrieved from http://www.oralcontraceptives.com/about_benefits.asp on Apr. 5, 2010.

Davis, A. J. et al., "Advances in Contraception," Obstet. Gynecol. Clin. North. Am., Sep. 2000, vol. 27, No. 3, pp. 597-610.

Conrad, J. et al., "Natural Estrogens for Oral Contraception," The Lancet, Sep. 1, 1979, pp. 471.

Moller, Svend E., "Deaths of Infants After Triple Vaccine," The Lancet, Sep. 1, 1979, pp. 472.

Carlborg, Lars, "Comparison of Contraception Acceptability of Levonorgestrel and Ethinyl Oestradiol Administered in one Three-Phasic (Trionetta) and one Monophasic (Neovletta) Version" Contraception, May 1983, vol. 27, No. 5, pp. 439-452.

Guenferich, Peter F., "Oxidation of 17 alpha-Ethynylestradiol by Human Liver Cytochrome p-450," Molecular Pharmacology, vol. 33, pp. 500-508, 1988.

Bocker, R. "In vitro interaction of contraception steroids with human liver cytochrome P-450 enzymes," Department of Toxicology and Pharmacology, University of Erlangen-Nurnberg, pp. 141-148, 1991.

Zhu, Bao Ting et al., "The Carcinogenic Activitiy of Ethinyl Estrogens Is Determined by Both Their Hormonal Characteristics and Their Conversion to Catechol Metabolites," Endocrinology, vol. 132, No. 2, 1993, pp. 577-583.

Hirvonen, E. et al., "Oral Contraceptives containing natural estradiol for premenopausal women," Maturitas, 1995, vol. 21, pp. 27-32.

Wenzl, Rene et al., "Ovulation inhibition with a combined oral contraceptive containing 1 mg micronized 17 beta-estradiol," Fertility and Sterility, Oct. 1993, vol. 60, No. 4, pp. 616-619.

Elstein, Max et al., "Studies on Low-dose oral contraceptives: Cervial mucus and plasma hormone changes in relation to circulating d-norgestrel and 17 alpha-ethynyl estradiol concentrations," Fertility and Sterility, Aug. 1976, vol. 27, No. 8, pp. 892-899.

Aktories, K. et al., "Die Beeinflussung des Ovarialzyklus durch verschiedene Typen hormonaler Kontrazeptiva," Geburtsch. U. Frauenheilk, 1976, vol. 36, pp. 318-326.

Zeun, S. et al., "Use of estradiolvalerate and dienogest for oral treatment of dysfunctional uterine bleeding in a contraceptive method," Publication Date: May 23, 2007; Retrieved from espacenet.com on May 26, 2010; English Abstract of EP1787649.

Opposition filed by Sandoz International GmbH against EP1787649 on Nov. 26, 2009.

English Translation of Opposition filed by Sandoz International GmbH against EP1787649 on Nov. 26, 2009.

Goretzlehner, G. et al., "Zur Nomenklatur der Zyklusstorungen," Frauenarzt, 2005, vol. 46, No. 1, pp. 34-37.

Tapanainen, J. S., "Medical management of menstrual disorders," International Congress Series, 2004, vol. 1266, pp. 63-68.

Golbs, S. et al., "Clinical Findings with the Oral Contraceptive Combination Ethinylestradiol/ Dienogest in Poland," Methods Find Exp Clin Pharmacol, 2002, vol. 24, No. 9, pp. 585-592.

Golbs, S. et al., "Clinical Findings with the Oral Contraceptive Combination Ethinylestradiol/ Dienogest in the Czech Republic," Methods Find Exp. Clin. Pharmacol., vol. 24, No. 10, pp. 689-696, 2002.

Mueck, A. O. et al., "Effect on biochemical vasoactive markers during postmenopausal hormone response replacement therapy: estradiol versus estradiol/dienogest," Maturitas, 2001, vol. 38, pp. 305-313.

Chuong, C.J., M.D., et al., "Management of abnormal uterine bleeding," Am. J. Obstet. Gynecol., Sep. 1996, pp. 787-792.

Durán, M., et al., "Efectividad de estradiol valerato/dienogest en la function sexual durante la menopausia (Estudio Venux)," Acta ginecologica, vol. LXIII, (2006) pp. 1-8.

Zimmerman, H., et al., "Toxicology of Dienogest," Drugs of Today, 1999, 35 (Suppl. C): pp. 13-26.

Pierson, R.A., et a l., "Ortho Evar™ /Evra™ versus oral contraceptives: follicular development and ovulation in normal cycles and after intentional dosing error," Fertility and Sterility, vol. 80, No. 1, Jul. 2003, pp. 34-42.

Chemical Translations, Dr. S. Edmund Berger, translation from German to English of U.S. Appl. No. 11/873,595, by S. Zeun, et al., 9 pages and certificate of Accuracy.

Akerlund, M. et al., "Comparative profiles of reliability, cycle control and side effects of two oral contraceptives formulations containing 150uh desogestrel and either 30 ug or 20 ug ethinyl oestradiol," British Journal of Obstetrics and Gynaecology, Sep. 1993, vol. 100, pp. 832-838.

Asche & Co AG C F., "Three-stage combination oral contraceptives—contg. Oestrogen with increasing doses of gestagen," Publication Date: Jan. 22, 1976; English Abstract of DE-2 431 704.

Astedt, B. et al., The natural oestrogenic hormone oestradiol as a new component of combined oral contraceptives, Br Med J, 1977.

Bayer, S. R. et al., "Clinical manifestations and treatment of dysfunctional uterine bleeding," JAMA, Apr. 14, 1993, vol. 269, No. 14.

Clinical Study Report No. A39818, visits from Mar. 2, 2005 to Jul. 20, 2007, Bayer Healthcare.

Darney, P. 1993, Contraception, pp. 323-337.

Darney, P., "Safety and efficacy of a triphasic oral contraceptive containing desogestrel: Results of three multicenter trials," Contraception, Oct. 1993, vol. 48, pp. 323-337.

Darney, P. D. et al., "Contraception-Associated menstrual Problems: Etiology and Managament," Dialogues in Contraception, 1998, vol. 5, No. 5.

Declaration by Maria de las Nieves Fernandez Hernando, Apr. 12, 2001.

Dittgen et al., U.S. Appl. No. 09/648,858 filed on Aug. 25, 2000, Amendment dated Dec. 22, 2003, 8 pages.

Dittgen et al., U.S. Appl. No. 09/950,915 filed Sep. 12, 2001, Amendment dated Dec. 18, 2003, 12 pages.

Dittgen et al., U.S. Appl. No. 09/950,915 filed Sep. 12, 2001, Amendment dated Aug. 19, 2004.

Dittgen et al., U.S. Appl. No. 08/738,314 filed Oct. 25, 1996; Declaration filed on Apr. 18, 2000.

Dittgen et al., U.S. Appl. No. 08/738314 filed Oct. 25, 1996; Amendment dated Jan. 7, 2000, 13 pages.

Drugs of the Future, 2001, vol. 26, No. 6, pp. 577-625.

Endrikat - Study 5, 10 pages, submitted Jan. 27, 2010.

Excerpts from 10/891,729 file history; Reasons for Allowance of Jun. 15, 2009; Amendment of Feb. 13, 2009, Jul. 22, 2008, and Oct. 18, 2004; Official Actions of Nov. 14, 2008 and Apr. 2, 2008; Terminal Disclaimer of Feb. 13, 2009.

Foster, R. H. et al., "Dienogest," Drugs, Nov. 1998, vol. 56, No. 5, pp. 825-833.

Graser, T. et al., "Organ targeting with the oral progestin dienogest," Drugs of Today, 1996, vol. 32, Suppl. H, pp. 43-55.

Hesslinger Hermann Dr Rer Nat., "Three-phase product for contraception composed of ethinylestradiol and lynestrenol," Data Retrieved from Espacenet Database, Publication Date: May 3, 1984; English Abstract of DE 3 341 638.

Hoffmann et al., Pharmakokinetik von Dienogest als monopraparat und in kombination mit ethinylestradiol, dienogest—praklinik und klinik eines gestagens, 2. Auflage, Herausgegeben von A. T. Teichmann, Walter de Gruyter, Berlin/New York, 1995, pp. 95-104.

Kwiecien, M. et al., "Bleeding patterns and patient acceptability of standard or continous dosing regimens of a low dose oral contraceptive: a randomized trial," Contraception, 2003, vol. 67, pp. 9-13.

Lox, C. D. et al., "Biochemical effects in women following one year's exposure to a new triphasic contraceptive—I. Chemistry Profiles," Gen. Pharmac., 1996, vol. 27, No. 2, pp. 367-370.

Miller et al., "Continuous combination oral contraceptives pills to eliminate withdrawal bleeding: A randomized trial," Obstetrics and Gynecology, Apr. 2003, vol. 101, No. 4, pp. 653-661.

Moore, C. et al., "Der Einfluss von Dienogest auf die Ovulation junger Frauen und auf ausgewahlte endokrinologische Parameter," Dienogest: Praklinik und Klinik . . ., 1995, pp. 161-170.

Package Insert Climodien, Mar. 23, 2006, 11 pages.

Public Assessment Report of the Medicines Evaluation Board, Qlaira, 2009.

Rosenbaum, P. et al., "Inhibition of ovulation by a novel progestogen (drospirenone) alone of in combination with ethinylestradiol," European Journal of Contraception and Reproductive Health Care, 2005, Vol. 5, pp. 16-24.

Schwarz, B. E. et al., "Reference period analysis of vaginal bleeding with triphasic oral contraceptive agents containing norethindrone of levonorgestrel: a comparison study," Int. J. Fertility, 1992, vol. 37, No. 3, pp. 176-182.

Sheth, A. et al., "Task Force on Oral Contraceptives," Contraception, 1982, vol. 25, No. 3, pp. 243-252.

Taubert, H. D. et al., Kontrazeption mit Hormonen, 1995, pp. 397-398.

Taubert, H. et al., Kontrazeption mit Hormonen, 1995, pp. 125-128.

Taubert, H. et al., Kontrazeption mit Hormonen, 1995, pp. 61-62.

Teichmann, A. et al., "Pharmacology of estradiol valerate/dienogest" Climacteric, 2003, vol. 6, Suppl. 2, pp. 17-23.

Tuimala, T. et al., "A clinical comparison in finland of two oral contraceptives containing 0.150 mg Desogestrel in combination with 0.020mg or 0.030 mg Ethinylestradiol," Acta Obstet Gynecol Scand Suppl., 1987, vol. 144, pp. 7-12.

Udoff et al., "Combined continuous hormone replacement therapy: A critical review," Obstetrics & Gynecology, Aug. 1995, vol. 86, No. 2.

Umbreit Klause Dr Med., "Ovulation-inhibiting composition for hormonal contraception," Data Retrieved from the Espacenet Database, Publication Date: Nov. 10, 1994; English Abstract of DE 4 339 934.

Unisearch Ltd., "Sequential oral contraceptive pack," Publication Date: Feb. 9, 1970; English Abstract of NL-6 911 920.

Wiegratz, I. et al., "Effect of four different oral contraceptives on various sex hormones and serum-binding globulins," Contraception, 2003, vol. 67, pp. 25-32.

Wright, J. V. et al., Comparative Measurements of Serum Estriol, Estradiol, and Estrone in Non-pregnant, Premenopausal Women: a Preliminary Investigation, Altern. Med. Rev. (U.S.), Aug. 1999, vol. 4, No. 4, pp. 266-270.

Zimmermann, T. et al., "The efficacy and tolerability of Valette: a postmarketing surveillance study," Eur J. Contracept. Reprod. Health Care, Septmeber 1999, vol. 4, No. 3, pp. 155-164.

Hoffmann, H., et al., Exp. Toxic Pathol. 1998; 50: 458-464.

Hoffmann, H., et al., Drugs of Today 1999; 35 (Suppl. C): 105-113.

Moore, C., et al. In: Kuhl, H., Nikolov, R., eds. Jenapharm GmbH & Co. KG 1998; 25-35.

* cited by examiner

COMBINATION PREPARATION FOR ORAL CONTRACEPTION AND ORAL THERAPY OF DYSFUNCTIONAL UTERINE BLEEDING CONTAINING ESTRADIOL VALERATE AND DIENOGEST AND METHOD OF USING SAME

CROSS-REFERENCE

This is a continuation-in-part of U.S. patent application Ser. No. 11/377,693, filed Mar. 16, 2006, which, in turn, claims the benefit of priority of invention under 35 U.S.C. 119 (e) based on U.S. Provisional Application, Ser. No. 60/727,592, filed Oct. 17, 2005.

BACKGROUND OF THE INVENTION

1. The Field of the Invention

The subject matter of the present invention comprises the use of estradiol valerate or estradiol in combination with 17α-cyanomethyl-17β-hydroxyestra-4, 9-dien-3-one (dienogest) to make a multiphase combination preparation for oral therapy of dysfunctional uterine bleeding and for oral contraception. This multiphase combination preparation contains a first phase of 2 daily dosage units, each consisting of 3 mg of estradiol valerate or less than 3 mg of estradiol; a second phase of two groups of daily dosage units, a first group of which consists of 5 daily dosage units, each consisting of a combination of 2 mg of dienogest with 2 mg of estradiol valerate or with less than 2mg of estradiol, and a second group of which consists of 17 daily dosage units, each consisting of a combination of 3 mg of dienogest with 2 mg of estradiol valerate or with less than 2 mg of estradiol; a third phase of 2 daily dosage units, each consisting of 1 mg of estradiol valerate or of less than 1 mg estradiol; and another phase of 2 daily dosage units of pharmaceutically harmless placebo, which contains a total number of 28 daily dosage units. The total number of daily dosage units of the multiphase combination preparation is sufficient for 28 days.

2. Description of the Related Art

Dysfunctional uterine bleeding (DUB) is a frequent clinical problem in gynecology and affects up to 33% of women presenting themselves for gynecological medical examinations on an outpatient basis (Awward J. T., Toth T. L., Schiff I., Abnormal Uterine Bleeding in the Perimenopause, Int. J. Fertil. 1993; 38, pp. 261-9). The symptoms of DUB are:
- extended menstrual bleeding (>7 days)
- frequent bleeding (interval between bleeding episodes of less than or equal to 21 days)
- increased bleeding (more than or equal to 80 ml).

DUB requires a diagnosis by exclusion, namely organic causes such as myoma, polyps or cancer must be excluded before a DUB diagnosis can be made.

DUB is associated with anovulation as well as ovulation. Such bleeding disturbances are due to an imbalance between the estrogen-stimulating build-up phase (proliferation) of the endometrium and the gestagenic transformation of the endometrium. If the DUB symptoms are a result of chronic anovulation, the endometrium is often exposed to increased gestagenic proliferation. Such proliferation can lead to hyperplasia of the endometrium besides the bleeding disturbances (Speroff, et al., Clinical Gynecologic Endocrinology and Infertility, sixth edition, Lippincott, Williams and Wilkins, 1999).

Hyperplasia of the endometrium is a risk factor for the onset of endometrial cancer.

Fraser, I. S., Aust. N Z J. Obstet. Gynaecol. (1990) 30 (4), pp. 353-356, reported the treatment of dysfunctional uterine bleeding by administration of 5 mg of norethisterone, three times daily, or 10 mg of medroxyprogesterone acetate, three times daily, as the only high-dosage gestagen, in each case for 14 days from the $12^{th}$ to the $25^{th}$ day of the cycle in 6 anovulatory women and for 20 days from the $5^{th}$, to the $25^{th}$ day of the cycle in ten ovulatory women. In both groups, the duration of the bleeding period was reduced. Reliable contraception was not attained.

Hickey M., Higham J. and Fraser I S, The Chochrane Library, Issue 3 2004 (Mickey M, Higham J, Fraser I S, Progestogens Versus Estrogens and Progestogens for Irregular Uterine Bleeding Associated with Anovulation (Cochrane Review), In The Cochrane Library, Issue 3 2004, Chichester, UK: John Wiley & Sons, Ltd) describe in a review article the low tolerance of women for irregular and extensive bleeding. They describe the rationale behind the use of gestagens to achieve a transformation of the endometrium and thus to create more stable menstruation cycles. The conclusion of the article is that clinical data from randomized studies demonstrating the efficacy of the described treatments are currently not available.

Steiner, R., Schweiz. Rundsch. Med. Prax. (2000) 91 (46), pp. 1967-1974, also points out that dysfunctional uterine bleeding should be treated with, among other methods, high-dosage gestagens, estrogens or a combination of both.

Steiner sees a treatment regimen in the oral administration of 0.01 mg of ethinyl estradiol with 2 mg of norethisterone acetate for 8 days in decreasing dosages, namely 6, 5, 4, 3, 3, 3, 3, 3/day. Besides the hormonal approach, Steiner postulates the possibility of treating an acute bleeding situation with tranexaminic acid, up to 4×2 tablets per day.

Davis, A., Obstet. Gynecol. (2000) 96 (6), pp. 913-920, describes the treatment of dysfunctional uterine bleedings by a three-step administration of ethinyl estradiol (EE)/norgestimate (NGM) followed by hormone-free administration of placebo for three 28-day cycles. According to the treatment regimen, the EE dosage remains constant over 21 days (0.035 mg of EE), the NGM dose increases over 21 days (7 daily dosage units of 0.180 mg of NMG and 7 daily dosage units of 0.215 mg of NMG and 7 daily dosage units of 0.250 mg of NMG), followed by a 7-day hormone-free placebo administration. The placebo-controlled study carried out by Davis included 45% of women with increased menstrual bleeding (metrorrhagia, menometrorrhagia and polymenorrhea) and about 55% of women with reduced menstrual bleeding (oligomenorrhea). The highest degree of success compared to placebo was achieved in women with reduced menstrual bleeding in whom regular withdrawal bleeding was induced. Oligomenorrhea is not necessarily a component of the DUB symptom group and is not recognized as an ailment worthy of treatment.

U.S. Pat. No. 6,782,282 discloses that generally extended use (3 months) of oral contraceptives can be used for the treatment of menorrhagia—a form of dysfunctional uterine bleeding.

SUMMARY OF THE INVENTION

The object of the present invention is to provide a multiphase combination preparation and a method for using it to treat dysfunctional uterine bleeding so that the extent of the bleeding is generally reduced and the recurrence of dysfunctional bleeding is generally prevented, while at the same time ensuring reliable, safe and well-tolerated oral contraception.

By the term "dysfunctional uterine bleeding" here means extended menstrual bleeding lasting more than 7 days with an interval between bleeding episodes of less than or equal to 21 days, or increased bleeding of more than or equal to 80 ml without an organic cause.

According to the invention this objective is attained by a multiphase combination preparation for oral therapy of dysfunctional uterine bleeding and for oral contraception, which is based on a combination of either estradiol valerate or estradiol with 17α-cyano-methyl-17β-hydroxyestra-4,9-dien-3-one (dienogest). The multiphase combination preparation contains a first phase of 2 daily dosage units, each consisting of 3 mg of estradiol valerate or of less than 3 mg estradiol; a second phase of 2 groups of daily dosage units, including a first group consisting of 5 daily dosage units, each consisting of a combination of 2 mg of dienogest with 2 mg of estradiol valerate or with less than 2 mg of estradiol, and a second group consisting of 17 daily dosage units, each consisting of a combination of 3 mg of dienogest with 2 mg of estradiol valerate or with less than 2 mg of estradiol; a third phase consisting of 2 daily dosage units, each consisting of 1 mg of estradiol valerate or less than 1 mg of estradiol and another phase of 2 daily dosage units of a pharmaceutically harmless placebo. The total number of daily dosage units of the multiphase combination preparation and the pharmaceutically harmless placebo should be sufficient for 28 days.

The duration of use comprises at least one treatment cycle and depends on the individual desires of the woman regarding contraception.

In a preferred embodiment of the multiphase combination preparation each daily dosage unit of the first phase consists of 2.25 mg of estradiol; each daily dosage unit of the second phase contains only 1.5 mg of estradiol; and each daily dosage units of the third phase consists of 0.75 mg of estradiol.

In another preferred embodiment of the multiphase combination preparation each daily dosage unit of the first phase consists of 3 mg of estradiol valerate; each daily dosage unit of the second phase contains 2 mg of estradiol valerate; and each daily dosage unit of the third phase consists of 1 mg of estradiol valerate.

STUDIES OF THE EFFICACY OF THE CLAIMED FORMATION 180 women 18 to 50 years of age with DUB symptoms, in whom an organic cause of the symptoms is excluded by appropriate diagnostic methods (transvaginal ultrasound, hormone determination in the blood) and who give their written consent to participate in the study, are treated in a randomized, double-blind, placebo-controlled clinical study. 120 women receive estradiol valerate and dienogest in accordance with the inventive combination and 60 women receive placebo.

The study comprises a run-in phase of 90 days during which the severity of the bleeding disturbances is recorded, 6 treatment cycles and one post-treatment cycle (follow-up phase).

The extent of bleeding is determined quantitatively by the alkaline hematin method. To this end, the women collect the monthly discharges during the entire study period and give them to the testing center. The duration of the bleeding and the duration of the bleeding-free intervals are recorded by daily documentation in an electronic journal.

While the invention has been illustrated and described as embodied in a combination preparation for oral contraception and oral therapy of dysfunctional uterine bleeding containing estradiol valerate and dienogest and method of using same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of treating dysfunctional uterine bleeding and of oral contraception, comprising orally administering to a woman in need of treatment for dysfunctional uterine bleeding and desiring oral contraception, over at least one treatment cycle of 28 days,
    one dosage unit comprising 3 mg of estradiol valerate daily for 2 days,
    then one dosage unit comprising 2 mg of estradiol valerate and 2 mg of dienogest daily for 5 days,
    then one dosage unit comprising 2 mg of estradiol valerate and 3 mg of dienogest daily for 17 days,
    then one dosage unit comprising 1 mg of estradiol valerate daily for 2 days, and
    then one dosage unit comprising a pharmaceutically acceptable placebo daily for 2 days.

2. The method of claim 1, comprising six of said treatment cycles of 28 days.

3. A method of treating dysfunctional uterine bleeding and of oral contraception, comprising orally administering to a woman in need of treatment for dysfunctional uterine bleeding and desiring oral contraception, over at least one treatment cycle of 28 days,
    a first phase of 2 daily oral dosage units, each comprising 3 mg of estradiol valerate,
    a second phase of 2 groups of daily oral dosage units, a first group comprising 5 daily oral dosage units, each of which comprises 2 mg of estradiol valerate and 2 mg of dienogest, and a second group comprising 17 daily oral dosage units, each of which comprises 2, mg of estradiol valerate and valerate and 3 mg of dienogest;
    a third phase of 2 daily oral dosage units, each comprising 1 mg of estradiol valerate, and
    a fourth phase of 2 daily oral dosage units, each comprising a pharmaceutically acceptable placebo.

4. The method of claim 3, comprising six of said treatment cycles of 28 days.

5. A method of treating dysfunctional uterine bleeding, comprising orally administering to a woman in need of treatment for dysfunctional uterine bleeding, over at least one treatment cycle of 28 days,
    a first phase of 2 daily oral dosage units, each comprising 3 mg of estradiol valerate,
    a second phase of 2 groups of daily oral dosage units, a first group comprising 5 daily oral dosage units, each of which comprises 2 mg of estradiol valerate and 2 mg of dienogest, and a second group comprising 17 daily oral dosage units, each of which comprises 2 mg of estradiol valerate and 3 mg of dienogest;
    a third phase of 2 daily oral dosage units, each comprising 1 mg of estradiol valerate, and
    a fourth phase of 2 daily oral dosage units, each comprising a pharmaceutically acceptable placebo.

6. The method of claim 5, comprising six of said treatment cycles of 28 days.

* * * * *

UNITED STATES PATENT AND TRADEMARK OFFICE
CERTIFICATE OF CORRECTION

PATENT NO. : 8,153,616 B2
APPLICATION NO. : 11/609705
DATED : April 10, 2012
INVENTOR(S) : Susan Zeun et al.

It is certified that error appears in the above-identified patent and that said Letters Patent is hereby corrected as shown below:

Title Page, Item (75) line 3 reads "Jan Nedrikat", should read --Jan Endrikat--

Signed and Sealed this
Twenty-fifth Day of June, 2013

Teresa Stanek Rea
*Acting Director of the United States Patent and Trademark Office*